US012769028B2

(12) United States Patent
Raman

(10) Patent No.: US 12,769,028 B2
(45) Date of Patent: Oct. 20, 2026

(54) HYDROCARBON PHASE BEHAVIOR MODELING FOR COMPOSITIONAL RESERVOIR SIMULATION

(71) Applicant: Saudi Arabian Oil Company, Dhahran (SA)

(72) Inventor: Vinay Raman, Lexington, MA (US)

(73) Assignee: Saudi Arabian Oil Company, Dhahran (SA)

( * ) Notice: Subject to any disclaimer, the term of this patent is extended or adjusted under 35 U.S.C. 154(b) by 1103 days.

(21) Appl. No.: 17/457,215

(22) Filed: Dec. 1, 2021

(65) Prior Publication Data

US 2023/0168409 A1 Jun. 1, 2023

(51) Int. Cl.

| | |
|---|---|
| ***G01V 20/00*** | (2024.01) |
| ***E21B 43/00*** | (2006.01) |
| ***G01N 33/24*** | (2006.01) |
| ***G06F 30/27*** | (2020.01) |

(Continued)

(52) U.S. Cl.

CPC .............. *G01V 20/00* (2024.01); *E21B 43/00* (2013.01); *G06F 30/27* (2020.01); *G06N 3/045* (2023.01); *E21B 2200/20* (2020.05); *E21B 2200/22* (2020.05); *G01N 33/241* (2013.01); *G16C 20/70* (2019.02)

(58) Field of Classification Search

CPC ..... G01V 20/00; E21B 43/00; E21B 2200/20; E21B 2200/22; E21B 41/00; G06F 30/20; G06F 30/27; G06F 2111/10; G06N 3/045; G06N 3/08; G01N 33/241; G16C 20/70; G16C 60/00; G16C 20/30

See application file for complete search history.

(56) References Cited

U.S. PATENT DOCUMENTS

| | | | | |
|---|---|---|---|---|
| 8,359,185 B2 | 1/2013 | Pita et al. | | |
| 9,372,943 B2 * | 6/2016 | Li | .......................... | G06T 17/05 |
| 10,767,475 B2 * | 9/2020 | Stone | ...................... | E21B 43/00 |

(Continued)

OTHER PUBLICATIONS

Ihunde, T. & Olorode, O. "Application of Physics Informed Neural Networks to Compositional Modelling" Unconventional Resources Technology Conference (Nov. 2021) (Year: 2021).*

(Continued)

*Primary Examiner* — Jay Hann

(74) *Attorney, Agent, or Firm* — Fish & Richardson P.C.

(57) ABSTRACT

Methods and systems for hydrocarbon phase behavior modeling for compositional reservoir simulation, the methods and systems configured for estimating phase properties of a hydrocarbon sample based on a mole-fraction weighted mixing rule; determining contributions of individual phase components to the mole-fraction weighted phase properties; generating input data for a machine learning model including a first sub-network and a second sub-network, the input data including the contributions from the phase properties; generating, based on processing the input data using the first sub-network of the machine learning model, probability values for each potential phase state; processing the probability values and input data by the second sub-network of the machine learning model; and generating, by the second sub-network, output data including equilibrium K-values, vapor fraction, vapor compressibility, and liquid compressibility for the hydrocarbon sample.

17 Claims, 9 Drawing Sheets

(51) Int. Cl.
*G06N 3/045* (2023.01)
*G16C 20/70* (2019.01)

(56) References Cited

U.S. PATENT DOCUMENTS

| | | | | |
|---|---|---|---|---|
| 10,781,686 | B2 * | 9/2020 | Wang | E21B 49/0875 |
| 10,859,730 | B2 | 12/2020 | Raman et al. | |
| 11,021,951 | B2 | 6/2021 | Olapade et al. | |
| 2019/0095792 | A1 | 3/2019 | Kashinath | |
| 2019/0227191 | A1 * | 7/2019 | Raman | G01N 33/241 |
| 2023/0352122 | A1 * | 11/2023 | Mawlod | G01N 33/2823 |
| 2024/0126959 | A1 * | 4/2024 | Ghorayeb | E21B 43/00 |

OTHER PUBLICATIONS

Lohrenz, J. "K-Values in the Reservoir" J. Canadian Petroleum Tech., vol. 6, No. 3, pp. 106-110, PETSOC-Mar. 5, 1967 (1967) (Year: 1967).*

Li et al., "Acceleration of the NVT Flash Calculation for Multicomponent Mixtures using Deep Neural Network Models" Ind. Eng. Chem. Res., 58, Jun. 2019, 12312-12322, 11 pages.

* cited by examiner

HYDROCARBON PHASE BEHAVIOR MODELING FOR COMPOSITIONAL RESERVOIR SIMULATION

TECHNICAL FIELD

The present specification generally relates to an approach for identifying geologic features in a subterranean formation.

BACKGROUND

In petroleum reservoir simulation, the composition of the reservoir fluids can be described using different models. In a black oil model, petroleum can be modeled as including one oil and one gas component. These components can be pseudo-components, in that they may not refer to any specific chemical components, such as methane or octane, but refer to a collection of components that can exhibit similar phase behavior. In compositional reservoir models, reservoir fluids can be described as a mixture of several pure chemical components, such as carbon dioxide ($CO_2$), hydrogen sulphide ($H_2S$), low-carbon alkanes (for example, methane and ethane), and pseudo-components for heavier hydrocarbons.

Compositional fluid models are increasingly used to simulate production from conventional reservoirs and fields developed using enhanced oil recovery techniques (EOR) (for example, surfactant flooding, polymer flooding, and miscible gas injection), since such models can be more accurate than traditionally used black oil models. In compositional models, reservoir fluid behavior can be generally modeled using an equation of state (EOS) and phase equilibrium calculations that require solving nonlinear systems of equations. These types of equations can be solved for phase stability analysis to determine the number of stable phases at equilibrium for a given composition, temperature, and pressure. If the stability analysis predicts that more than one phase is present, a nonlinear system of equations may also be solved in a phase-split (or flash) calculation to determine the mole fraction of all the phases present and the molar composition of each phase. Both stability and flash calculations may be performed once in every simulation cell at every time step. Therefore, the calculations can account for a major fraction of the total simulation time for up to 70%. As the spatial and temporal resolution of reservoir simulations increases, the computational costs associated with determining the phase behavior may also increase.

SUMMARY

The present specification describes systems and processes for determining hydrocarbon phase behavior for hydrocarbons for compositional reservoir simulation. Phase equilibrium determination for hydrocarbon phases containing 10 or more components generally can consume up to 40% of computing resources for reservoir simulation. The systems and processes described herein include a deep neural network (DNN) model that improves a speed of simulation relative to conventional processes for phase determination, reduces an amount computing resources used for hydrocarbon phase determination, and that also maintains an accuracy of the compositional reservoir simulation relative to conventional processes.

A data processing system includes a multi-class classification model and a regression model to form a DNN. The DNN includes a set of hidden layers (e.g., 1-7) and includes two sub-networks. A first sub-network identifies a phase state of a given grid block of a subsurface as being a liquid, a vapor, a two-phase state, or a critical state. A second sub-network performs the phase-split calculations for the grid block identified with two-phase state.

The subject matter described in this specification can be implemented in particular implementations, so as to realize one or more of the following advantages. In some implementations, the data processing system, using the DNN, is configured to generate features that represent physics of a phase equilibrium process. The features include K-values (e.g., equilibrium ratio values for respective components), vapor fraction values, liquid compressibility, vapor compressibility, and the phase state of the reservoir. The described DNN enables faster prediction times. For example, prediction generate time is reduced from 95.5 microseconds (for a model without the DNN) to 3.75 microseconds (e.g., using the DNN described herein). The model output accuracy is comparable or improved relative to reservoir simulations without the described DNN. For example, $F_1$ score, a metric of accuracy of the model, is 0.998 for the described DNN. The DNN is further optimized for parallelization for reducing computing output values representing the reservoir composition. For example, parallelization of the DNN on eight processing modules (e.g., computing cores) can reduce the prediction time to 0.46 microseconds from the described 3.75 microseconds.

The data processing system and DNN described herein enable an integrated machine learning model network for performing both phase identification and phase split determination. The combination of each of the phase identification and phase split determination enables a more accurate calculation of each of the phase identification and phase split determination than when these are performed individually. Furthermore, a training time of the DNN model is reduced by about 40%-50% because there is only one DNN to train, rather than multiple DNNs to train. This also reduces an amount of training data required for training the DNN in comparison to a non-integrated DNN.

Each of these advantages are enabled by one or more of the following embodiments.

In a general aspect, a process for hydrocarbon phase behavior modeling for compositional reservoir simulation includes the following operations. The operations include estimating phase properties of a hydrocarbon sample based on a mole-fraction weighted mixing rule; determining contributions of individual phase components to the mole-fraction weighted phase properties; generating input data for a machine learning model including a first sub-network and a second sub-network, the input data including the contributions from the phase properties; generating, based on processing the input data using the first sub-network of the machine learning model, probability values for each potential phase state; processing the probability values and input data by the second sub-network of the machine learning model; and generating, by the second sub-network, output data including equilibrium K-values, vapor fraction, vapor compressibility, and liquid compressibility for the hydrocarbon sample.

In some implementations, the operations include receiving training data comprising phase properties values; determining a categorical cross-entropy error from the first sub-network; generating a probabilities vector based on the probability values and the categorical cross-entropy error; processing the probability vector by the second sub-network; determining, based on the processing, a mean-squared error (MSE) between predicted output values and output values of the output data; and training the first sub-network and the second sub-network simultaneously by minimizing the MSE value over a plurality of training epochs.

In some implementations, the operations include generating the training data comprising the phase properties values by performing operations comprising: selecting a grid block for a simulated reservoir; for the selected grid block: generating input data of mole fractions based on a uniform distribution for pressure at a specified reservoir temperature; determining a stability value and a split-phase value for the generated mole-fraction data at each specified temperature and pressure; determining a phase state value based on the stability value and the split-phase value; and generating one or more of a vapor fraction value, a vapor compressibility value, a liquid compressibility value, and liquid fraction value based on the phase state value.

In some implementations, the input data further comprises a grid-block temperature a grid-block pressure, and mole fractions data.

In some implementations, the phase properties include a critical temperature a critical pressure, a critical volume, an acentric factor, a molecular weight value.

In some implementations, the hydrocarbon sample represents one of a five component sample, a seven component sample, or a nine component sample.

In some implementations, the machine learning model comprises a deep neural network (DNN) having at least three hidden layers and at least one output layer.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method/the instructions stored on the non-transitory, computer-readable medium.

The details of one or more embodiments are set forth in the accompanying drawings and the description below. Other features and advantages will be apparent from the description and drawings, and from the claims.

BRIEF DESCRIPTION OF THE DRAWINGS

Like reference numbers and designations in the various drawings indicate like elements.

DETAILED DESCRIPTION

Figure 1:
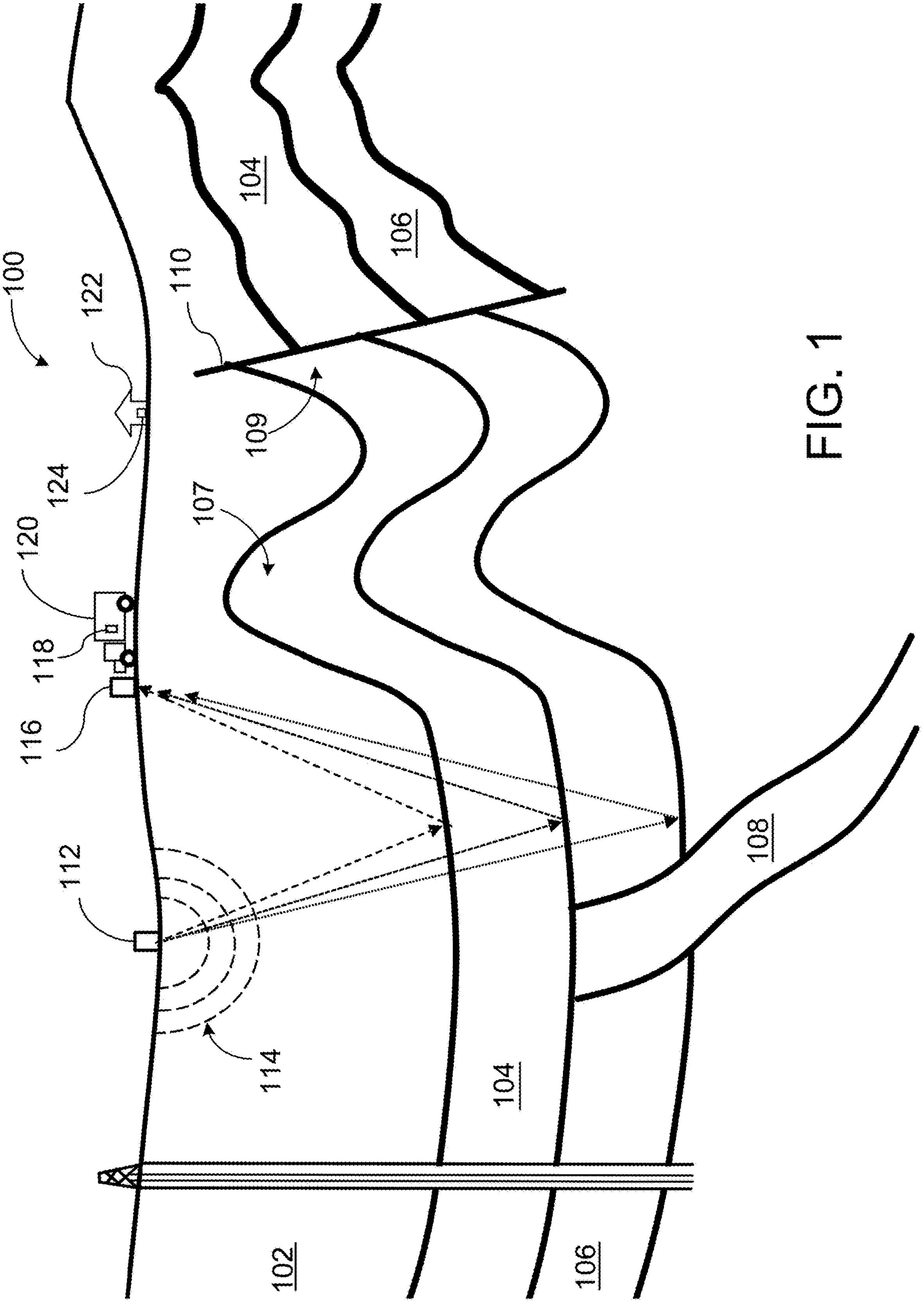
FIG. 1 is a schematic view of a seismic survey being performed to map subterranean features such as facies and faults.

The following specification describes systems and processes for determining hydrocarbon phase behavior for hydrocarbons for compositional reservoir simulation. Various modifications, alterations, and permutations of the disclosed implementations can be made and will be readily apparent to those of ordinary skill in the art, and the general principles defined may be applied to other implementations and applications, without departing from scope of the specification. In some instances, details unnecessary to obtain an understanding of the described subject matter may be omitted so as to not obscure one or more described implementations with unnecessary detail and inasmuch as such details are within the skill of one of ordinary skill in the art. The present specification is not intended to be limited to the described or illustrated implementations, but to be accorded the widest scope consistent with the described principles and features.

A data processing system described herein is configured for training and executing deep neural network (DNN) that is configured to perform each of phase identification and phase split for performing a hydrocarbon reservoir simulation. The hydrocarbon reservoir is part of a subsurface region that can be mapped using seismic imaging, as described herein.

The DNN includes a number of hidden layers. In an example, the DNN includes up to 7 hidden layers. The DNN includes two sub-networks. A first sub-network of the DNN is configured to identify a phase state of a given grid block. Phase states include a liquid phase, a vapor phase, a two-phase state, or a critical phase state. A second sub-network is configured to perform phase-split calculations for grid blocks identified as being or including a two-phase state.

The phase identification ability of the DNN is evaluated using precision, recall and $F_1$-scores. Precision (e.g., a positive predictive value) includes a fraction of relevant instances of data among available (e.g., identified) instances. Recall (e.g., sensitivity) is a fraction of relevant instances that are identified. Both precision and recall are therefore based on relevance. The $F_1$ score is the harmonic mean of the precision and recall. The DNN enables high $F_1$ scores ranging from 0.997 to 0.998 for different fluids characterizations tested. The phase-split sub-network is evaluated using percent absolute average relative deviation (AARD) for the equilibrium coefficients, vapor fraction, liquid and vapor compressibility. A low AARD is obtained for the equilibrium coefficients (e.g., less than 1.2%) and liquid/vapor compressibility (e.g., less than 1.1%). The DNN of the data processing system is configured for executing about 50% to 155% (depending on the computational load) faster over non-integrated DNNs that do not include a combination of the first and second sub-networks. To train the deep neural network, the data processing system uses input features that include contributions of individual components to the mixture critical temperature, mixture critical pressure, mixture critical acentric factor, and mixture molecular weight, as subsequently described.

FIG. 1 is a schematic view of a seismic survey being performed to map subterranean features such as facies and faults in a subterranean formation 100. The seismic survey can provide the underlying basis for implementation of the systems and methods described with reference to FIGS. 4A-4B. The subterranean formation 100 includes a layer of impermeable cap rocks 102 at the surface. Facies underlying the impermeable cap rocks 102 include a sandstone layer 104, a limestone layer 106, and a sand layer 108. A fault line 110 extends across the sandstone layer 104 and the limestone layer 106.

Oil and gas tend to rise through permeable reservoir rock until further upward migration is blocked, for example, by the layer of impermeable cap rock 102. Seismic surveys attempt to identify locations where interaction between layers of the subterranean formation 100 are likely to trap oil and gas by limiting this upward migration. For example, FIG. 1 shows an anticline trap 107, where the layer of impermeable cap rock 102 has an upward convex configuration, and a fault trap 109, where the fault line 110 might allow oil and gas to flow along with clay material between the walls traps the petroleum. Other traps include salt domes and stratigraphic traps.

A seismic source 112 (for example, a seismic vibrator or an explosion) generates seismic waves 114 that propagate in the earth. The velocity of these seismic waves depends on several properties, for example, density, porosity, and fluid content of the medium through which the seismic waves are traveling. Different geologic bodies or layers in the earth are distinguishable because the layers have different properties and, thus, different characteristic seismic velocities. For example, in the subterranean formation 100, the velocity of seismic waves traveling through the subterranean formation 100 will be different in the sandstone layer 104, the limestone layer 106, and the sand layer 108. As the seismic waves 114 contact interfaces between geologic bodies or layers that have different velocities, the interfaces reflect some of the energy of the seismic wave and refracts some of the energy of the seismic wave. Such interfaces are sometimes referred to as horizons.

The seismic waves 114 are received by a sensor or sensors 116. Although illustrated as a single component in FIG. 1, the sensor or sensors 116 are typically a line or an array of sensors 116 that generate output signals in response to received seismic waves including waves reflected by the horizons in the subterranean formation 100. The sensors 116 can be geophone-receivers that produce electrical output signals transmitted as input data, for example, to a computer 118 on a seismic control truck 120. Based on the input data, the computer 118 may generate a seismic data output, for example, a seismic two-way response time plot.

A control center 122 can be operatively coupled to the seismic control truck 120 and other data acquisition and wellsite systems. The control center 122 may have computer facilities for receiving, storing, processing, and analyzing data from the seismic control truck 120 and other data acquisition and wellsite systems. For example, computer systems 124 in the control center 122 can be configured to analyze, model, control, optimize, or perform management tasks of field operations associated with development and production of resources such as oil and gas from the subterranean formation 100. Alternatively, the computer systems 124 can be located in a different location than the control center 122. Some computer systems are provided with functionality for manipulating and analyzing the data, such as performing seismic interpretation or borehole resistivity image log interpretation to identify geological surfaces in the subterranean formation or performing simulation, planning, and optimization of production operations of the wellsite systems.

In some embodiments, results generated by the computer system 124 may be displayed for user viewing using local or remote monitors or other display units. One approach to analyzing seismic data is to associate the data with portions of a seismic cube representing the subterranean formation 100. The seismic cube can also be display results of the analysis of the seismic data associated with the seismic survey.

Figure 2:
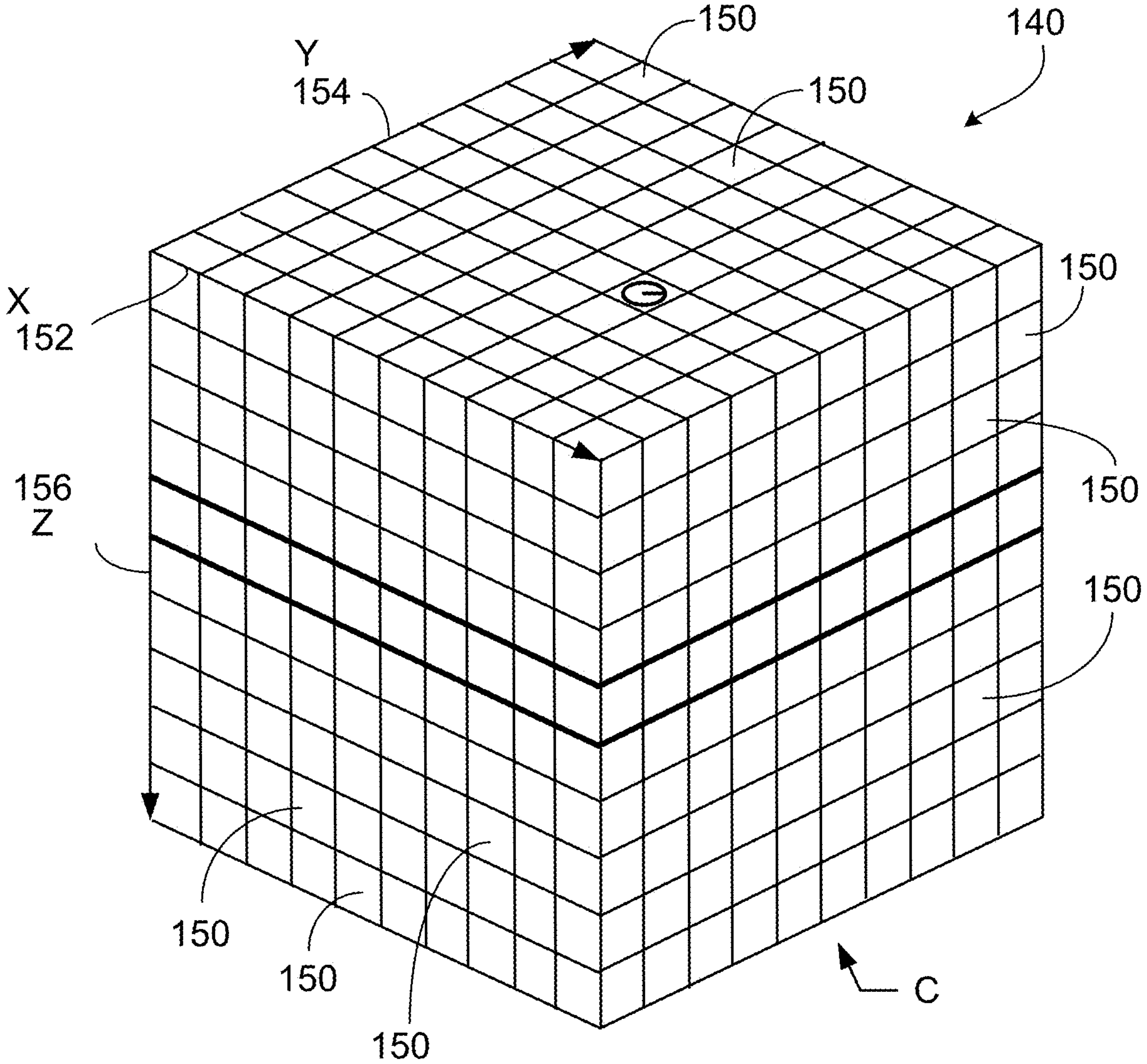
FIG. 2 illustrates a three-dimensional cube representing a subterranean formation.

FIG. 2 illustrates a seismic cube 140 representing at least a portion of the subterranean formation 100. The seismic cube 140 is composed of a number of voxels 150. A voxel is a volume element, and each voxel corresponds, for example, with a seismic sample along a seismic trace. The cubic volume C is composed along intersection axes of offset spacing times based on a delta-X offset spacing 152, a delta-Y offset spacing 154, and a delta-Z offset spacing 156. Within each voxel 150, statistical analysis can be performed on data assigned to that voxel to determine, for example, multimodal distributions of travel times and derive robust travel time estimates (according to mean, median, mode, standard deviation, kurtosis, and other suitable statistical accuracy analytical measures) related to azimuthal sectors allocated to the voxel 150.

Figure 3:
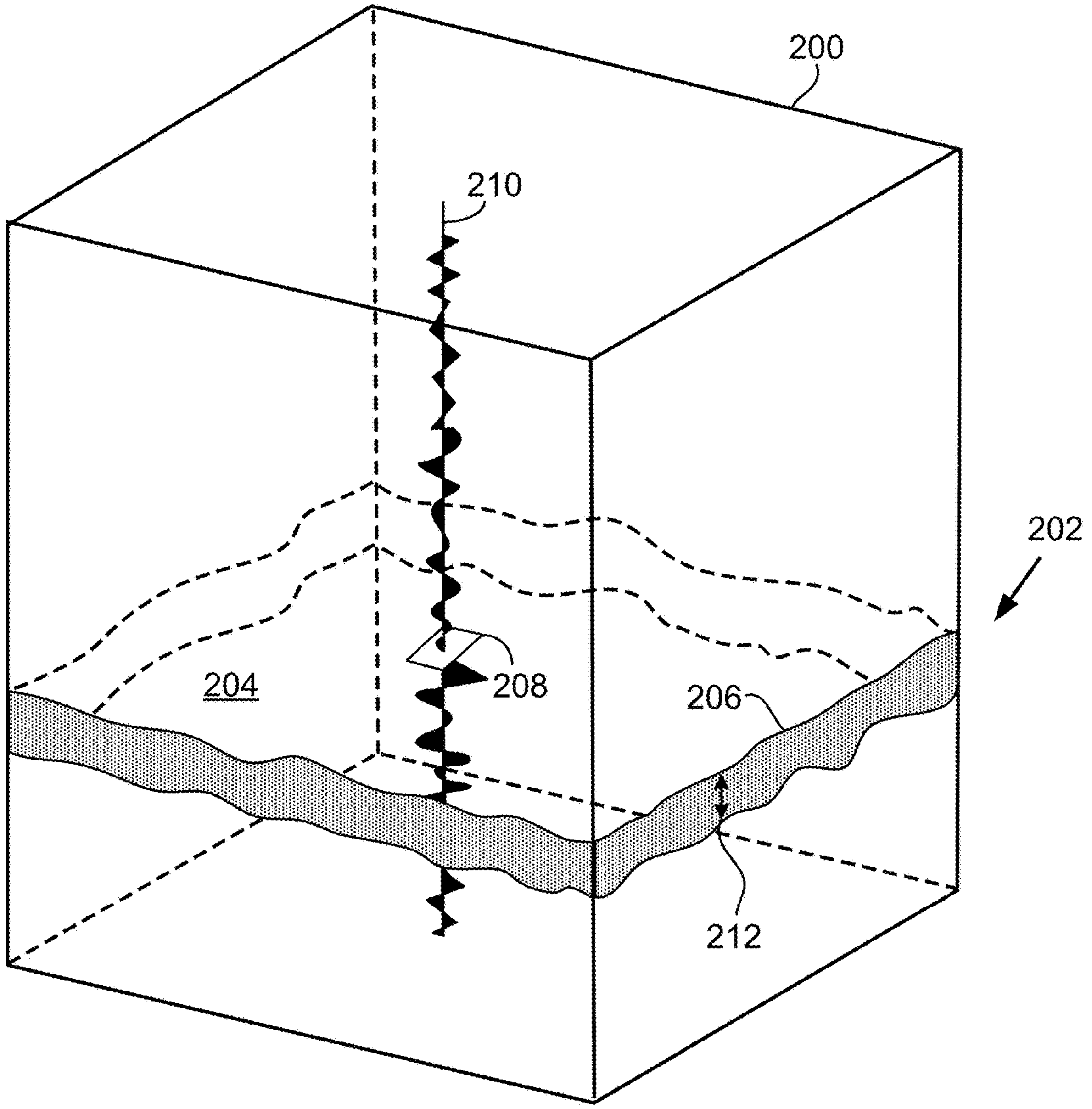
FIG. 3 illustrates a stratigraphic trace within the three-dimensional cube of FIG. 2.

FIG. 3 illustrates a seismic cube 200 representing a formation. The seismic cube has a stratum 202 based on a surface (for example, amplitude surface 204) and a stratigraphic horizon 206. The amplitude surface 204 and the stratigraphic horizon 206 are grids that include many cells such as exemplary cell 208. Each cell is a seismic trace representing an acoustic wave. Each seismic trace has an x-coordinate and a y-coordinate, and each data point of the trace corresponds to a certain seismic travel time or depth (t or z). For the stratigraphic horizon 206, a time value is determined and then assigned to the cells from the stratum 202. For the amplitude surface 204, the amplitude value of the seismic trace at the time of the corresponding horizon is assigned to the cell. This assignment process is repeated for all of the cells on this horizon to generate the amplitude surface 204 for the stratum 202. In some instances, the amplitude values of the seismic trace 210 within window 212 by horizon 206 are combined to generate a compound amplitude value for stratum 202. In these instances, the compound amplitude value can be the arithmetic mean of the positive amplitudes within the duration of the window, multiplied by the number of seismic samples in the window.

Figure 4:
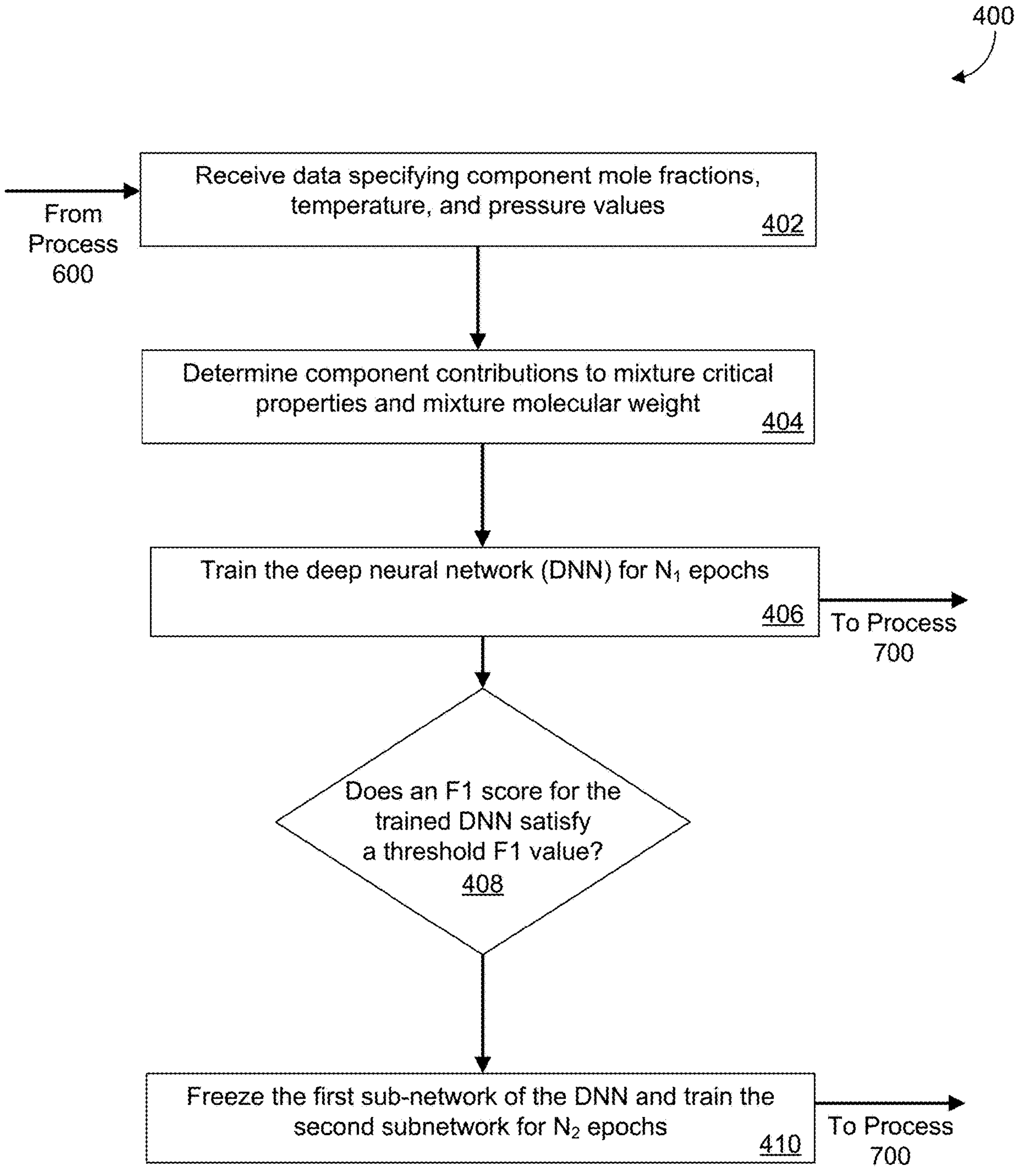
FIG. 4 is a flowchart of an example of a process for hydrocarbon phase behavior modeling for compositional reservoir simulation.

FIG. 4 is a flowchart of an example of a process 400 for hydrocarbon phase behavior modeling for compositional reservoir simulation, according to some implementations of the present specification. For clarity of presentation, the description that follows generally describes process 400 in the context of the other figures in this description. However, it will be understood that process 400 can be performed, for example, by any suitable system, environment, software, and hardware, or a combination of systems, environments, software, and hardware, as appropriate. In some implementations, various steps of process 400 can be run in parallel, in combination, in loops, or in any order.

The data processing system is configured to receive (402) phase data specifying component mole fractions, temperature, and pressure values. As subsequently described, the component mole fractions include phase property data for an analyzed grid block (e.g., block 150 of FIG. 2). The data processing system is configured to analyze the phase property data from the grid block and classify the phase state of the grid block The phase properties for a given overall mole-fraction of grid-block ($z_i$) include the phase properties ($T_C$, $P_C$, $V_C$, ω, $M_w$) of an oil sample using a mole-fraction weighted mixing rule that includes the following:

$$T_{C,mix} = \sum_{i=1}^{nc} T_{C,i};\ P_{C,mix} = \sum_{i=1}^{nc} P_{C,i};\ V_{C,mix} = \sum_{i=1}^{nc} V_{C,i};$$

$$M_{w,mix} = \sum_{i=1}^{nc} M_{w,i};\ \text{and}\ \omega_{mix} = \sum_{i=1}^{nc} \omega_i.$$

Here, $T_c$ is a critical temperature, $P_c$ is a critical pressure, $V_c$ is a critical volume, ω is the acentric factor, and Mw is molecular weight. The acentric factor includes measure of the non-sphericity (centricity) of molecules. The critical pressure, critical temperature, and critical volume are the respective pressures, temperatures, and volumes for the hydrocarbon in the grid cell at critical points for the hydrocarbon. Here, the critical point (or critical state) is the end point of a phase equilibrium curve for the hydrocarbon. For each phase property type, a summation is performed for the property values for each component i.

The data processing system is configured to determine (404) the component contributions to mixture critical properties and mixture molecular weight for the phase properties. As subsequently described in relation to FIG. 7, to obtain the contribution of each of the individual components, the data processing system is configured to find ratios between a value for each phase property ($T_C$, $P_C$, $V_C$, ω, $M_w$) at each component with the summed value of the phase property for the mixture. This illustrates the relative contribution of each individual component to the mole-fraction weighted phase properties. The relationships include the following:

$$T_i = \frac{T_{C,i}}{T_{C,mix}};\ P_i = \frac{P_{C,i}}{P_{C,mix}};\ M_i = \frac{M_{w,i}}{M_{w,mix}};\ \omega_i = \frac{\omega_i}{\omega_{mix}};\ V_i = \frac{V_{c,i}}{V_{C,mix}},$$

where $T_{c,i}$ is the critical temperature for a respective component i, where $P_{c,i}$ is the critical pressure for the respective component i, where $M_i$ is the molecular weight for the respective component i, where $\omega_i$ is the acentric factor for the respective component i, and where $V_{c,i}$ is the critical volume for the respective component i.

The data processing system is configured to train (406) the DNN for a given number $N_1$ epochs. Here, an epoch refers to an iteration through the entire training dataset. In some implementations, the number $N_1$ is set at an upper limit. The DNN is trained until a training metric is satisfied (e.g., the $F_1$ score exceeds a minimum). In some implementations, the DNN is trained until the number $N_1$ is reached. The $F_1$ score is subsequently described in further detail and represents an accuracy score for the classification of the phase state for given grid blocks.

The data processing system determines (408) if the $F_1$ score satisfies the threshold. If so, the data processing system freezes (410) the training of the first subnetwork and trains the second sub-network, as described in relation to FIG. 7.

Figure 5:
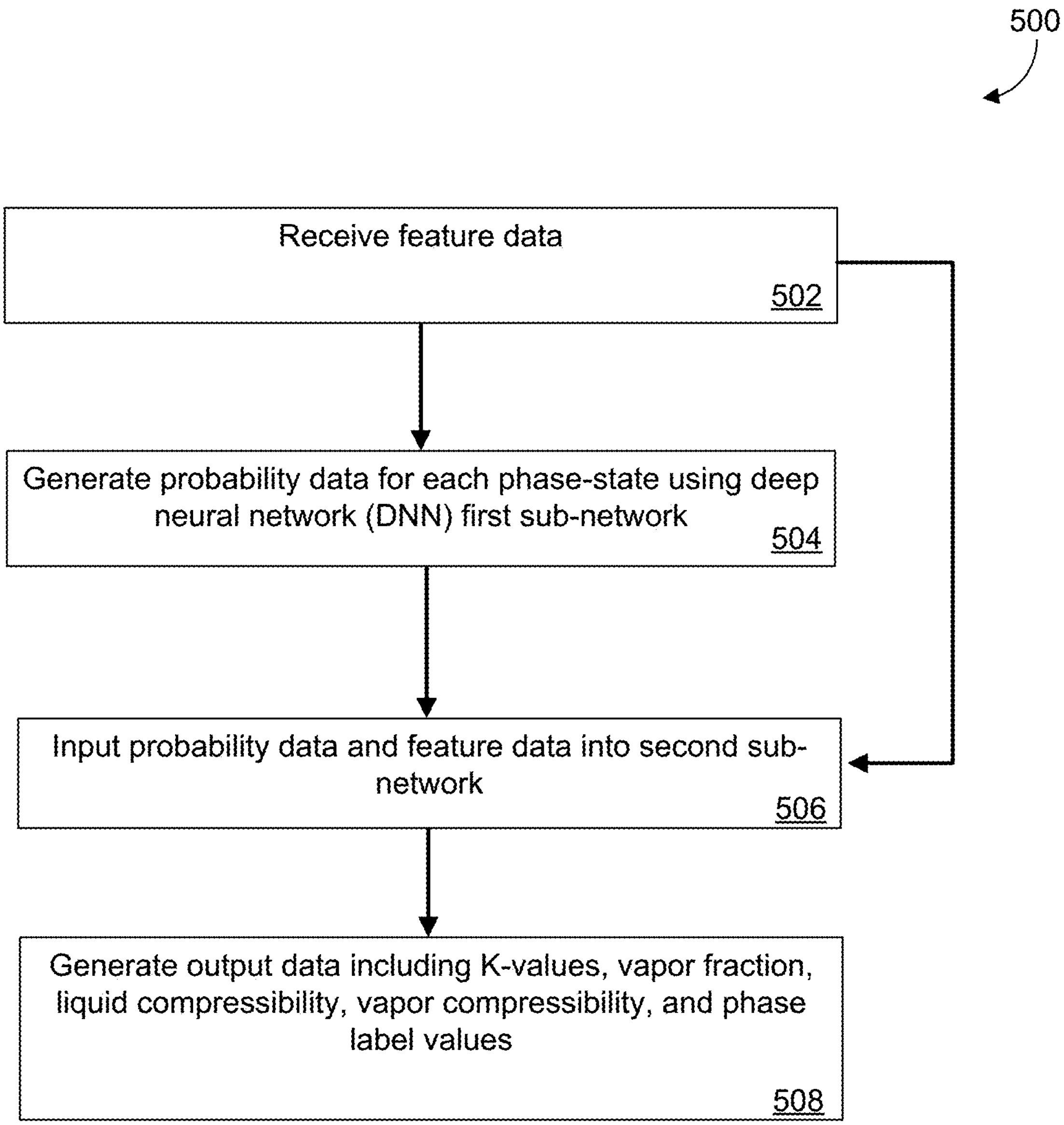
FIG. 5 is a flowchart of an example of a process for hydrocarbon phase behavior modeling for compositional reservoir simulation.

FIG. 5 is a flowchart of an example of a process 500 for hydrocarbon phase behavior modeling for compositional reservoir simulation, according to some implementations of the present specification. For clarity of presentation, the description that follows generally describes process 500 in the context of the other figures in this description. However, it will be understood that process 500 can be performed, for example, by any suitable system, environment, software, and hardware, or a combination of systems, environments, software, and hardware, as appropriate. In some implementations, various steps of process 400 can be run in parallel, in combination, in loops, or in any order.

The process 500 includes executing the trained DNN on phase property data for grid blocks (e.g., blocks 150 of FIG. 2) for a subsurface region. The process 500 enables the data processing system to simulate a reservoir in a region and determine phase states for each grid block of the subsurface region. The process 500 includes receiving (502) feature data including the phase property data and mole-mixture values as described herein. The data processing system is configured to generate (504) probability data for each phase state for a given grid block using the trained DNN. The data processing system is configured to input (506) the generated probabilities data and the feature data into the second sub-network. The data processing system, using the trained second sub-network, is configured to generate (508) output data including K-values, vapor fraction values, liquid compressibility values, vapor compressibility values, and phase label values for the grid block. The data processing system can output the phase probability values in addition to the other phase property values. These outputs can be useful for downstream reservoir simulation applications.

Figure 6:
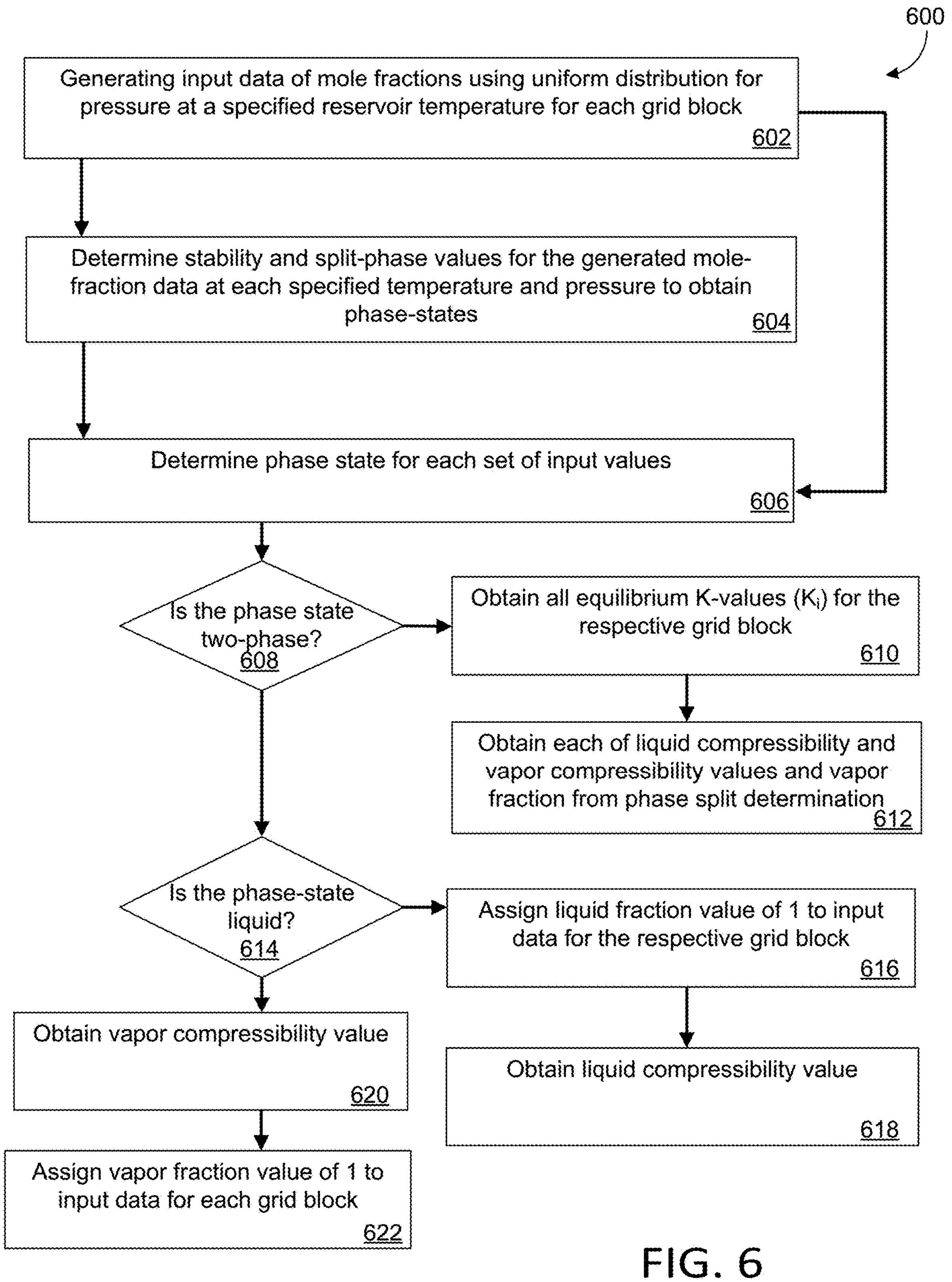
FIG. 6 shows a process for generating training data for the first and second sub-networks of the DNN described previously such as in relation to FIGS. 4-5.

FIG. 6 shows a process 600 for generating training data for the first and second sub-networks of the DNN described previously such as in relation to FIGS. 4-5. For clarity of presentation, the description that follows generally describes process 600 in the context of the other figures in this description. However, it will be understood that process 600 can be performed, for example, by any suitable system, environment, software, and hardware, or a combination of systems, environments, software, and hardware, as appropriate. In some implementations, various steps of process 600 can be run in parallel, in combination, in loops, or in any order. Generally, the process 600 is executed by the data processing system described herein.

The process 600 includes generating (602) input data of mole-fractions (e.g., from 0 to 1) using a Dirichlet distribution for each grid block (e.g., blocks 150 of FIG. 2). The input data also includes a uniform distribution for pressure from a minimum pressure $P_{min}$ to a maximum pressure $P_{max}$. The pressure distribution is associated with a specified reservoir temperature ($T_R$).

The data processing system determines (604) stability and phase-split values for the generated mole-fraction input data. Each of the stability values and the phase-split values are determined for each given temperature and associated pressure(s) of the input data. The data processing system determines phase-states for each set of input values.

Generally, determining stability and phase split values is performed using a process having two steps. The first step includes a stability calculation to determine the number of phases present. The second step includes a phase-split calculation using an equation of state to solve for the composition of each phase. The stability calculation is used to determine whether a phase-split calculation is necessary or not. Generally, the stability calculation is performed by determining a test composition for a new test phase (an initial guess). The stability calculation includes determining a chemical potential of the existing phase. The stability calculation includes determining, from the chemical potential and the test composition, a composition of the new test phase such that the chemical potentials of the test phase and existing phase are equal (such as by using an equation of state). If the compositions of all test phases result in an increase in the Gibbs free energy, the existing phase is stable. If the compositions of all test phases do not result in an increase in the Gibbs free energy, then a phase-split calculation is used to determine the composition of the new phase.

The steps for the phase split calculation are as follows. In a first step, if the system is unstable, the system performs an estimate of the partition coefficient K from the stability calculation are used to generate the initial guess for the phase-split calculation. Using these initial guesses, a Newton-Raphson method is used to solve material balance and equilibrium relations that are generated using an equation of state. Generally, this system is iterated until convergence is obtained. The resulting convergence yields the vapor and liquid fractions, as well as the composition of each species in each phase.

The data processing system determines (606) a phase state for each set of values. The phase state can include a liquid phase state, a vapor phase state, a two-phase equilibrium, or a critical state. The data processing system determines (608) if the phase state is a two-phase state for a respective grid block. If the phase state is a two-phase state including both liquid and vapor, the data processing system obtains (610) all equilibrium K values ($K_i$) for the respective grid block. The data processing system obtains (612) each of a liquid compressibility value and a vapor compressibility value for the respective grid block. If the data processing system determines that the phase state is not a two-phase state, each of the K-values is set to zero for including in the training data.

The data processing system determines (614) whether the phase state is a liquid phase state. If the phase state is a liquid phase state, the data processing system assigns a vapor fraction value of 0 to the respective grid block and assigns (616) a liquid fraction value of 1 to the respective grid block. The data processing system obtains (618) a liquid compressibility value for the respective grid block for including in the training data. If the data processing system determines that the phase state is not a liquid state but a vapor state, the data processing system obtains (620) the vapor compressibility value for the respective grid block for including the training data and assigns (622) a vapor fraction value of 1 to the respective grid block for including in the training data.

Figure 7:
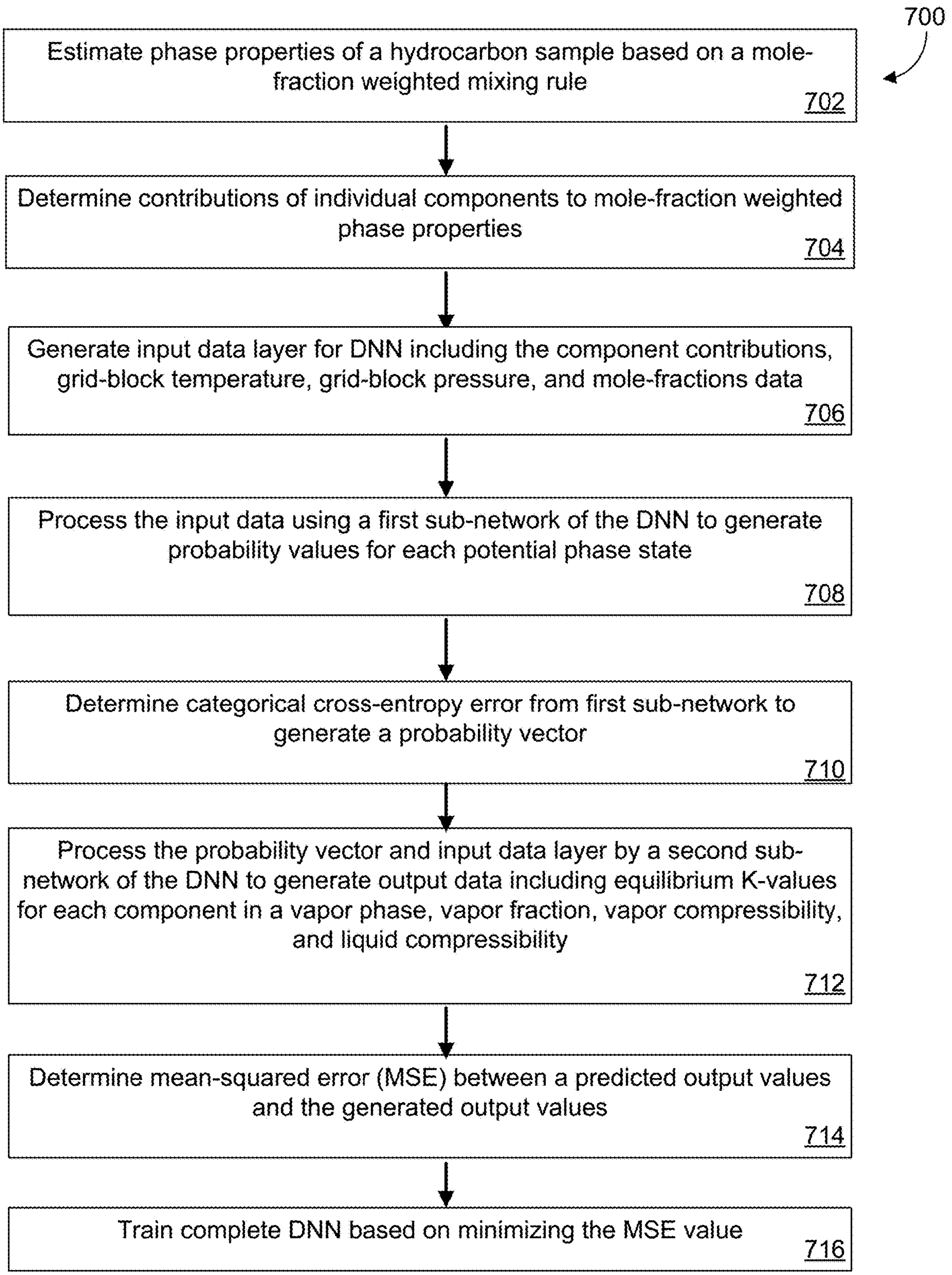
FIG. 7 shows a process for feature generation and training the DNN by the data processing system.

FIG. 7 shows a process 700 for feature generation and training the DNN by the data processing system. The DNN is trained with training data that is generated by the process 600 previously described in relation to FIG. 6. The DNN can include the DNN described previously such as in relation to FIGS. 4-5. For clarity of presentation, the description that follows generally describes process 700 in the context of the other figures in this description. However, it will be understood that process 700 can be performed, for example, by any suitable system, environment, software, and hardware, or a combination of systems, environments, software, and hardware, as appropriate. In some implementations, various steps of process 700 can be run in parallel, in combination, in loops, or in any order. Generally, the process 700 is executed by the data processing system described herein.

The data processing system is configured to estimate (702) phase properties of a hydrocarbon sample based on a mole-fraction weighted mixing rule. To estimate the phase properties, the data processing system, for a given overall mole-fraction of grid-block ($z_i$), determines the phase properties ($T_C$, $P_C$, $V_C$, ω, $M_w$) of an oil sample using a mole-fraction weighted mixing rule that includes the following:

$$T_{C,mix} = \sum_{i=1}^{nc} T_{C,i};\ P_{C,mix} = \sum_{i=1}^{nc} P_{C,i};\ V_{C,mix} = \sum_{i=1}^{nc} V_{C,i};$$
$$M_{w,mix} = \sum_{i=1}^{nc} M_{w,i};$$

and $$\omega_{mix} = \sum_{i=1}^{nc} \omega_i.$$

Here, $T_c$ is a critical temperature, $P_c$ is a critical pressure, $V_c$ is a critical volume, ω is the acentric factor, and Mw is molecular weight. The acentric factor includes measure of the non-sphericity (centricity) of molecules. The critical pressure, critical temperature, and critical volume are the respective pressures, temperatures, and volumes for the hydrocarbon in the grid cell at critical points for the hydrocarbon. Here, the critical point (or critical state) is the end point of a phase equilibrium curve for the hydrocarbon. For each phase property type, a summation is performed for the property values for each component i.

The data processing system is configured to determine (704) contributions of individual components to mole-fraction weighted phase properties. To obtain the contribution of each of the individual components, the data processing system is configured to find ratios between a value for each phase property ($T_C$, $P_C$, $V_C$, ω, $M_w$) at each component with the summed value of the phase property for the mixture. This illustrates the relative contribution of each individual component to the mole-fraction weighted phase properties. The relationships include the following:

$$T_i = \frac{T_{C,i}}{T_{C,mix}};\ P_i = \frac{P_{C,i}}{P_{C,mix}};\ M_i = \frac{M_{w,i}}{M_{w,mix}};\ \omega_i = \frac{\omega_i}{\omega_{mix}};\ V_i = \frac{V_{c,i}}{V_{C,mix}},$$

where $T_{c,i}$ is the critical temperature for a respective component i, where $P_{c,i}$ is the critical pressure for the respective component i, where $M_i$ is the molecular weight for the respective component i, where $\omega_i$ is the acentric factor for the respective component i, and where $V_{c,i}$ is the critical volume for the respective component i.

The data processing system is configured to generate (706) data for an input data layer of the DNN. The input data includes each of the component contributions for phase properties ($T_C$, $P_C$, $V_C$, ω, $M_w$), the grid-block temperature T, the grid-block pressure P, and mole-fractions $z_i$ data. The data processing system process (708) the input data using the first sub-network of the DNN to generate probability values for each potential phase state (e.g., liquid, vapor, two-phase, or critical phase states). The number of phase states can also include other phase states such as surfactant phase, dispersed phase, water phase, $CO_2$-rich phase-state, $CO_2$-lean phase-state, and so forth.

The data processing system is configured to determine (710) a categorical cross-entropy error based on the probability values generated by the first sub-network. The categorical cross-entropy error is based on equation (1)

$$CrossEntropy = -\sum_{k=1}^{N_p} p_k^{true} \log(p_k^{pred}), \tag{1}$$

where $$p_k^{true}$$

is the indicator function for true phase-state such that $$p_k^{true}=1$$

if the true phase-state is k, else $$p_k^{true}=0.$$

In addition, $N_p$ is the number of phases formed in system, and $$p_k^{pred}$$

is the probability for the phase-state k predicted by first sub-network.

The data processing system is configured to process (712) the probability vector and input data layer by a second sub-network of the DNN to generate output data including equilibrium K-values for each component in a vapor phase, vapor fraction, vapor compressibility, and liquid compressibility. More specifically, the data processing system uses a probability vector of dimension $N_p$, $$\{p_k^{true}\}_{i=1\ to\ \mathrm{Np}}$$

along with the input layer of first sub-network as a second input layer to the second sub-network. The output of the second sub-network includes equilibrium K-values, $K_i$, of component i in vapor phase, vapor-fraction (β), and the compressibility values for the liquid phases ($Z_x$) and vapor phases ($Z_y$).

The data processing system is configured to determine a mean-squared error (MSE) between a predicted output values and the generated output values, as shown in equation (2):

$$MSE=\sum_{i=1}^{nc}\left(K_i^{true}-K_i^{pred}\right)^2+\left(Z_x^{true}-Z_x^{pred}\right)^2+\left(Z_y^{true}-Z_y^{pred}\right)^2+\left(\beta^{true}-\beta^{pred}\right)^2, \tag{2}$$

where $$K_i^{true} \text{ and } K_i^{pred}$$

are the respective generated and predicted values for component respectively, where $$Z_x^{true} \text{ and } Z_x^{pred}$$

are the respective generated and predicted compressibility values for the liquid phase, where $$Z_y^{true} \text{ and } Z_y^{pred}$$

are the respective generated and predicted compressibility values for the vapor phase, and where $\beta^{true}-\beta^{pred}$ are the generated and predicted vapor fraction values, respectively.

The data processing system is configured to train (716) the complete deep-learning network in order to minimize the total error based on equation (3):

$$\text{Total error}=CrossEntropy+MSE \tag{3}$$

By minimizing the total error of the DNN output, both the first and second sub-networks are trained simultaneously.

The data processing system is configured to train the first and second sub-networks for a specified number of epochs, which indicates a number of complete passes through the training dataset. The data processing system iterates through the training dataset until the $F_1$ score obtained from the first sub-network satisfies an acceptance threshold, as described in relation to FIG. 4. The data processing system then freezes the weights of the first sub-network while continuing to train the second sub-network by minimizing only the mean-squared error until a threshold is satisfied, as previously described in relation to FIG. 4. In some implementations, the number of epochs for the first and second sub-network together is set at 300, the $F_1$ threshold is set at 0.995, and the number of epochs for the second sub-network is set at 200. These are example values, and other thresholds or epoch values are possible.

A number of example experiments for generating and testing the DNN are now described. Each of these experiments is a particular example for validating the DNN and illustrating functionality of the DNN. These examples are not exhaustive or comprehensive.

In a first experiment, a five component fluid is modeled with the fluid characterization shown in Table 1.

TABLE 1

Fluid Characterization of a Five Component Fluid

| Component | $T_c$ | $P_c$ | Acentric factor | $V_c$ | $M_w$ |
|---|---|---|---|---|---|
| $CO_2$ | 304.14 | 73.75 | 0.239 | 2.14e−3 | 44.0 |
| $C_1$ | 190.56 | 45.99 | 0.011 | 6.15e−3 | 16.0 |
| $C_2$ | 305.32 | 48.72 | 0.099 | 4.84e−3 | 30.1 |
| $C_3$ | 369.83 | 42.48 | 0.153 | 4.54e−3 | 44.1 |
| $C_6$ | 507.4 | 30.12 | 0.296 | 4.22e−3 | 86.2 |

For this experiment, the data processing system uses synthetic data based on standard flash calculations. The temperature is fixed at 400 degrees Kelvin, and the pressure is varied from 70 bar to 400 bar. A Dirichlet distribution is used to sample the overall mole-fractions of the components ranging from 0 to 1. About 1 million data points are generated for training and an additional 300,000 data points are generated for testing.

In this experiment, the DNN includes the following architecture. The first sub-network includes three hidden layers having 30, 20, and 10 neurons respectively. The hidden layers include leaky-relu activation functions. The leaky-relu function includes a modified rectified linear unit function. The rectified linear units (e.g., ReLU) is a type of activation function that is linear in a positive dimension and zero in a negative dimension. The leaky ReLU is a ReLU having a small slope for negative values instead of a flat slope. The slope coefficient is determined before training, such that it is not learned during training.

The output layer includes a softmax activation function. The softmax activation function takes as input the vector z of K real numbers, and normalizes it into a probability distribution consisting of K probabilities proportional to the exponentials of the input numbers. Specifically, the output of the first sub-network is a softmax layer that gives probabilities for the different phases.

In this experiment, the second sub-network includes 4 hidden layers having 128, 64, 32, and 16 neurons respectively. A leaky-relu activation function is used for all the hidden layers. There is no activation for the output layer.

This experiment included 1 million data points for training the DNN. The data processing system generates 46 features by applying the first sub-network based on step 708 described in relation to FIG. 7. The data processing system trains both the networks simultaneously for about 300 epochs or until the first sub-network achieves $F_1$ score satisfying a threshold (e.g., 0.995). The data processing system freezes the weights of the first sub-network and further trains the second sub-network for an additional 200 epochs or until the MSE becomes less than $1\times10^{-6}$.

The data processing system optimizes the DNN using an optimizer. In some implementations, the Adam optimizer is used. This optimizer includes an adaptive learning rate method configured to compute individual learning rates for different parameters. The optimizer uses estimations of first and second moments of gradient to adapt the learning rate for each weight of the neural network.

The data processing system performs hyper-parameter tuning by having a schedule for the learning rate. Initially, a learning rate of $1\times10^{-3}$ is used, and this is subsequently reduced by a factor of 0.1 after 50, 100 and 150 epochs respectively. After 300 epochs, the learning rate is reduced from $1\times10^{-5}$ by a factor of 0.1 after each of 100 and 150 epochs. Thus, the last 50 epochs of training each have a learning rate of $1\times10^{-7}$. L2 regularization (e.g., having $\alpha$=0.001) is used for the hidden layers in the second sub-network. The model can be easily extended to include other hyper-parameter tuning techniques such as L1 regularization, dropout layers, batch-normalization, and so forth.

In this experiment, the DNN is tested on 300,000 test data points that are generated as previously described. The pressure range of the test data points is within the 70-400 bar interval. The temperature is fixed at 400 K. A Dirichlet distribution is used to sample overall mole-fractions of the components. The accuracy of the phase identification by the DNN is as follows. A precision is 0.99871388. A recall is 0.99919802. An $F_1$ score is 0.99895572. The classification rate is 99.95%. These are example metrics from this experiment and are illustrative of the accuracy of the described DNN.

In a second experiment, a seven component fluid is modeled with the fluid characterization shown in Table 2.

TABLE 2

Fluid Characterization of a Seven Component Fluid

| Component | $T_c$ | $P_c$ | Acentric-factor | $V_c$ | Mw |
|---|---|---|---|---|---|
| CO2 | 304.14 | 73.75 | 0.239 | 2.14e−3 | 44.0 |
| C1 | 190.56 | 45.99 | 0.011 | 6.15e−3 | 16.0 |
| C2 | 305.32 | 48.72 | 0.099 | 4.84e−3 | 30.1 |
| C3 | 369.83 | 42.48 | 0.153 | 4.54e−3 | 44.1 |
| nC4 | 425.12 | 37.96 | 0.199 | 4.39e−3 | 58.1 |
| nC5 | 469.70 | 33.70 | 0.251 | 4.31e−3 | 72.2 |

For this experiment, the data processing system uses synthetic data based on standard flash calculations. The temperature is fixed at 400 degrees Kelvin, and the pressure is varied from 70 bar to 400 bar. A Dirichlet distribution is used to sample the overall mole-fractions of the components ranging from 0 to 1. About 1 million data points are generated for training and an additional 300,000 data points are generated for testing.

In this experiment, the DNN includes the following architecture. The first sub-network includes three hidden layers having 42, 28, and 14 neurons, respectively. The hidden layers include leaky-relu activation function, previously described in relation to the first experiment. The output layer includes a softmax activation function. The output of the first sub-network is a softmax layer that gives probabilities for the different phases, as previously described in relation to the first experiment.

In this experiment, the second sub-network includes 4 hidden layers having 160, 80, 40, and 20 neurons, respectively. A leaky-relu activation function is used for all the hidden layers. There is no activation for the output layer. The first and second sub-networks in the second experiment are trained as described in relation to FIG. 7.

In this experiment, the DNN is tested on 300,000 test data points that are generated as previously described. The pressure range of the test data points is within the 70-400 bar interval. The temperature is fixed at 400 K. A Dirichlet distribution is used to sample overall mole-fractions of the components. The accuracy of the phase identification by the DNN is as follows. A precision is 0.99862629. A recall is 0.99914591. An $F_1$ score is 0.99888589. The classification rate is 99.94%. These are example metrics from this experiment and are illustrative of the accuracy of the described DNN.

In a third experiment, a nine component fluid is modeled with the fluid characterization shown in Table 3.

TABLE 3

Fluid Characterization of a Nine Component Fluid

| Component | $T_c$ | $P_c$ | Acentric-factor | $V_c$ | $M_w$ |
|---|---|---|---|---|---|
| CO2 | 304.14 | 73.75 | 0.239 | 2.14e−3 | 44.0 |
| C1 | 190.56 | 45.99 | 0.011 | 6.15e−3 | 16.0 |
| C2 | 305.32 | 48.72 | 0.099 | 4.84e−3 | 30.1 |
| C3 | 369.83 | 42.48 | 0.153 | 4.54e−3 | 44.1 |
| iC4 | 407.80 | 36.04 | 0.183 | 4.46e−3 | 58.1 |
| nC4 | 425.12 | 37.96 | 0.199 | 4.39e−3 | 58.1 |
| nC5 | 469.70 | 33.70 | 0.251 | 4.31e−3 | 72.2 |
| nC6 | 507.40 | 30.12 | 0.296 | 4.22e−3 | 86.2 |

For this experiment, the data processing system uses synthetic data based on standard flash calculations. The temperature is fixed at 400 degrees Kelvin, and the pressure is varied from 70 bar to 400 bar. A Dirichlet distribution is used to sample the overall mole-fractions of the components ranging from 0 to 1. About 1 million data points are generated for training and an additional 300,000 data points are generated for testing.

In this experiment, the DNN includes the following architecture. The first sub-network includes three hidden layers having 54, 36, and 18 neurons, respectively. The hidden layers include leaky-relu activation function, previously described in relation to the first experiment. The output layer includes a softmax activation function. The output of the first sub-network is a softmax layer that gives probabilities for the different phases, as previously described in relation to the first experiment.

In this experiment, the second sub-network includes 4 hidden layers having 144, 96, 48, and 24 neurons, respectively. A leaky-relu activation function is used for all the hidden layers. There is no activation for the output layer. The first and second sub-networks in the second experiment are trained as described in relation to FIG. 7.

In this experiment, the DNN is tested on 300,000 test data points that are generated as previously described. The pressure range of the test data points is within the 70-400 bar interval. The temperature is fixed at 400 K. A Dirichlet distribution is used to sample overall mole-fractions of the components. The accuracy of the phase identification by the DNN is as follows. A precision is 0.99856701. A recall is 0.99871154. An $F_1$ score is 0.99863925. The classification rate is 99.95%. These are example metrics from this experiment and are illustrative of the accuracy of the described DNN.

Figure 8:
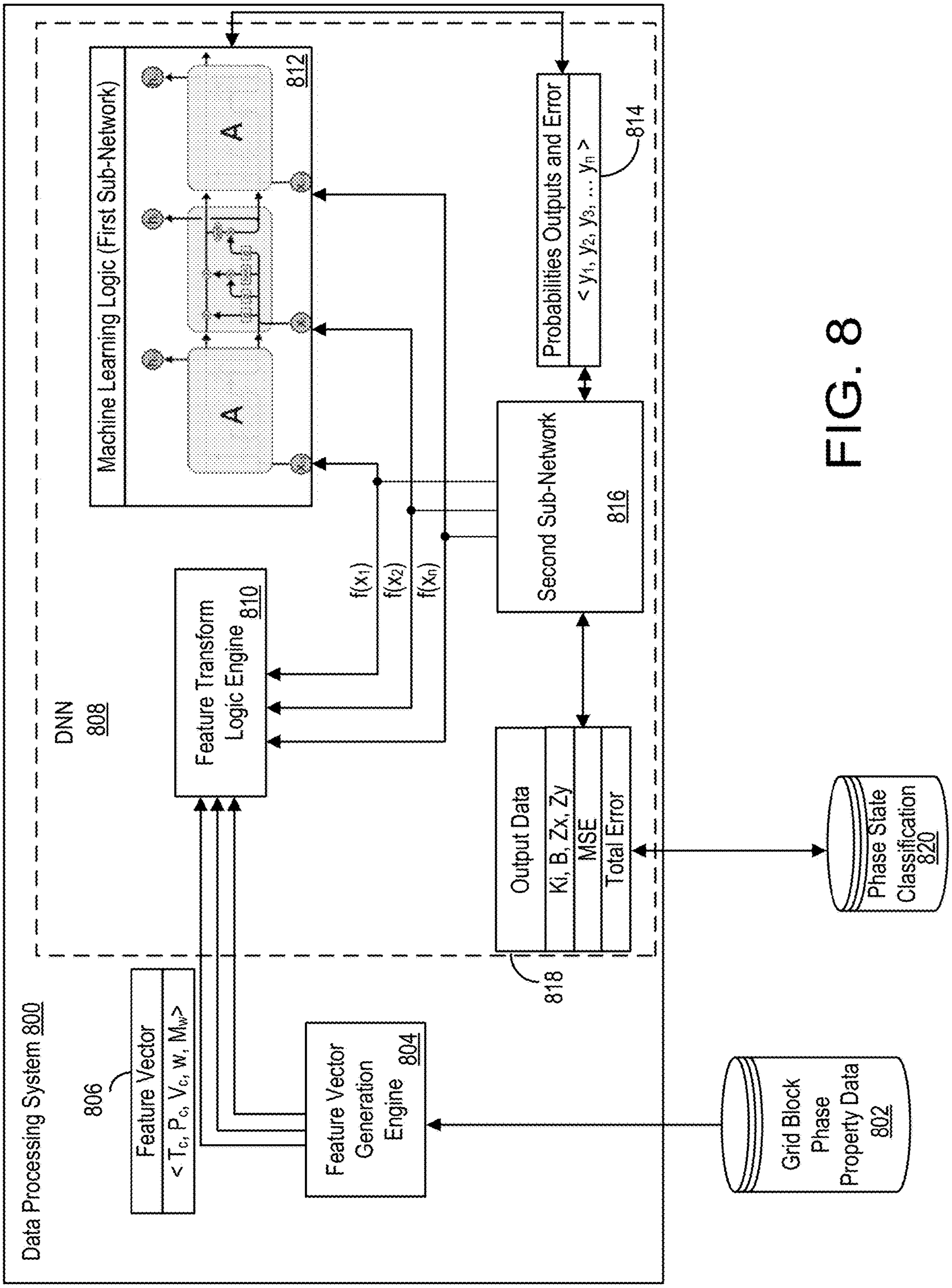
FIG. 8 shows an example data processing system configured to perform the processes described in this specification, including the processes described in FIGS. 4-7

FIG. 8 shows an example data processing system 800 configured to perform the processes described in this specification, including the processes described in FIGS. 4-7. The data processing system 800 is configured to execute a DNN 808 that includes a first sub-network 812 and a second sub-network 816, previously described. The data processing system 800 receives grid block phase property data from a data source 802. The feature vector generation engine 804 generates a feature vector 806 including the component contributions for phase properties as described in relation to FIG. 7. The feature transform logic engine 810 configures the phase properties vector 806 to be feature data that is input into the first layer of the first sub-network 812 of the DNN 808. The first sub-network 812 outputs the probabilities data 814 for each phase state in addition to a cross entropy error, as previously described. The error data and probabilities outputs 814 are input data into a second sub-network 816 that receives the feature data 806 as well, as previously described. The second sub-network outputs the output data 818 including the equilibrium K-values, $K_i$, of component i in vapor phase, vapor-fraction (β), and the compressibility values for the liquid phases ($Z_x$) and vapor phases ($Z_y$). The data processing system 800 also determines a MSE and total error as part of the output data 818 during training of the DNN 808. These error data are used to train the DNN 808 to improve the classification accuracy. The output data including the phase state classification data are stored in a data store 820 for use by one or more downstream applications for reservoir simulation.

Figure 9:
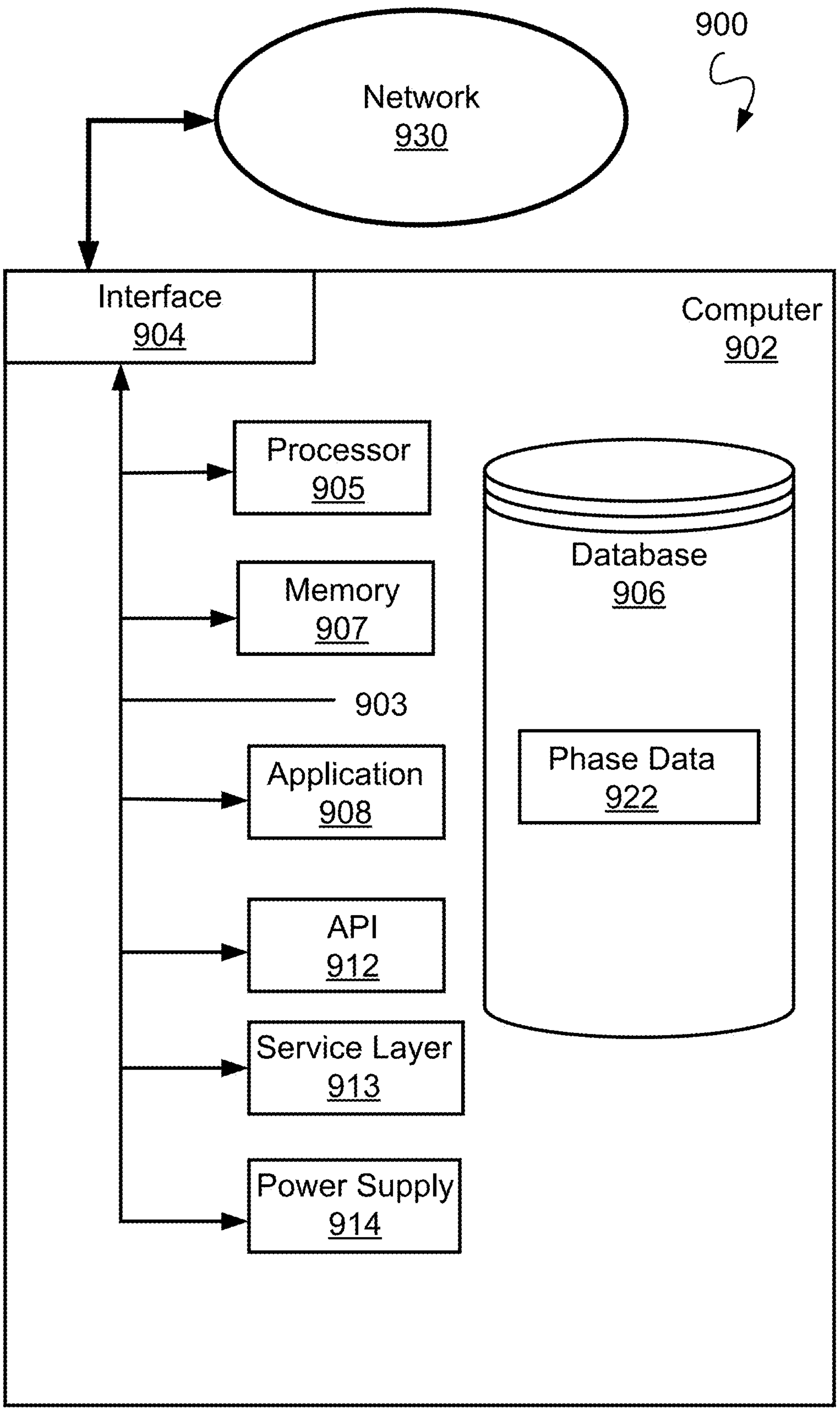
FIG. 9 is a block diagram illustrating an example computer system used to provide computational functionalities associated with described algorithms, methods, functions, processes, flows, and procedures as described in the present specification, according to some implementations of the present specification.

FIG. 9 is a block diagram of an example computer system 900 used to provide computational functionalities associated with described algorithms, methods, functions, processes, flows, and procedures described in the present specification, according to some implementations of the present specification such as the data processing system 800 described in relation to FIG. 8. The illustrated computer 902 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 902 can include input devices such as keypads, keyboards, and touch screens that can accept user information. Also, the computer 902 can include output devices that can convey information associated with the operation of the computer 902. The information can include digital data, visual data, audio information, or a combination of information. The information can be presented in a graphical user interface (UI) (or GUI).

The computer 902 can serve in a role as a client, a network component, a server, a database, a persistency, or components of a computer system for performing the subject matter described in the present specification. The illustrated computer 902 is communicably coupled with a network 930. In some implementations, one or more components of the computer 902 can be configured to operate within different environments, including cloud-computing-based environments, local environments, global environments, and combinations of environments.

At a top level, the computer 902 is an electronic computing device operable to receive, transmit, process, store, and manage data and information associated with the described subject matter. According to some implementations, the computer 902 can also include, or be communicably coupled with, an application server, an email server, a web server, a caching server, a streaming data server, or a combination of servers.

The computer 902 can receive requests over network 930 from a client application (for example, executing on another computer 902). The computer 902 can respond to the received requests by processing the received requests using software applications. Requests can also be sent to the computer 902 from internal users (for example, from a command console), external (or third) parties, automated applications, entities, individuals, systems, and computers.

Each of the components of the computer 902 can communicate using a system bus 903. In some implementations, any or all of the components of the computer 902, including hardware or software components, can interface with each other or the interface 904 (or a combination of both) over the system bus 903. Interfaces can use an application programming interface (API) 912, a service layer 913, or a combination of the API 912 and service layer 913. The API 912 can include specifications for routines, data structures, and object classes. The API 912 can be either computer-language independent or dependent. The API 912 can refer to a complete interface, a single function, or a set of APIs.

The service layer 913 can provide software services to the computer 902 and other components (whether illustrated or not) that are communicably coupled to the computer 902. The functionality of the computer 902 can be accessible for all service consumers using this service layer. Software services, such as those provided by the service layer 913, can provide reusable, defined functionalities through a defined interface. For example, the interface can be software written in JAVA, C++, or a language providing data in extensible markup language (XML) format. While illustrated as an integrated component of the computer 902, in alternative implementations, the API 912 or the service layer 913 can be stand-alone components in relation to other components of the computer 902 and other components communicably coupled to the computer 902. Moreover, any or all parts of the API 912 or the service layer 913 can be implemented as child or sub-modules of another software module, enterprise application, or hardware module without departing from the scope of the present specification.

The computer 902 includes an interface 904. Although illustrated as a single interface 904 in FIG. 9, two or more interfaces 904 can be used according to particular needs, desires, or particular implementations of the computer 902 and the described functionality. The interface 904 can be used by the computer 902 for communicating with other systems that are connected to the network 930 (whether illustrated or not) in a distributed environment. Generally, the interface 904 can include, or be implemented using, logic encoded in software or hardware (or a combination of software and hardware) operable to communicate with the network 930. More specifically, the interface 904 can include software supporting one or more communication protocols associated with communications. As such, the network 930 or the interface's hardware can be operable to communicate physical signals within and outside of the illustrated computer 902.

The computer 902 includes a processor 905. Although illustrated as a single processor 905 in FIG. 9, two or more processors 905 can be used according to particular needs, desires, or particular implementations of the computer 902 and the described functionality. Generally, the processor 905 can execute instructions and can manipulate data to perform the operations of the computer 902, including operations using algorithms, methods, functions, processes, flows, and procedures as described in the present specification.

The computer 902 also includes a database 906 that can hold data for the computer 902 (such as phase state data 922 of data stores 802, 820 of FIG. 8) and other components connected to the network 930 (whether illustrated or not). For example, database 906 can be an in-memory, conventional, or a database storing data consistent with the present specification. In some implementations, database 906 can be a combination of two or more different database types (for example, hybrid in-memory and conventional databases) according to particular needs, desires, or particular implementations of the computer 902 and the described functionality. Although illustrated as a single database 906 in FIG. 9, two or more databases (of the same, different, or combination of types) can be used according to particular needs, desires, or particular implementations of the computer 902 and the described functionality. While database 906 is illustrated as an internal component of the computer 902, in alternative implementations, database 906 can be external to the computer 902.

The computer 902 also includes a memory 907 that can hold data for the computer 902 or a combination of components connected to the network 930 (whether illustrated or not). Memory 907 can store any data consistent with the present specification. In some implementations, memory 907 can be a combination of two or more different types of memory (for example, a combination of semiconductor and magnetic storage) according to particular needs, desires, or particular implementations of the computer 902 and the described functionality. Although illustrated as a single memory 907 in FIG. 9, two or more memories 907 (of the same, different, or combination of types) can be used according to particular needs, desires, or particular implementations of the computer 902 and the described functionality. While memory 907 is illustrated as an internal component of the computer 902, in alternative implementations, memory 907 can be external to the computer 902.

The application 908 can be an algorithmic software engine providing functionality according to particular needs, desires, or particular implementations of the computer 902 and the described functionality. For example, application 908 can serve as one or more components, modules, or applications. Further, although illustrated as a single application 908, the application 908 can be implemented as multiple applications 908 on the computer 902. In addition, although illustrated as internal to the computer 902, in alternative implementations, the application 908 can be external to the computer 902.

The computer 902 can also include a power supply 914. The power supply 914 can include a rechargeable or non-rechargeable battery that can be configured to be either user- or non-user-replaceable. In some implementations, the power supply 914 can include power-conversion and management circuits, including recharging, standby, and power management functionalities. In some implementations, the power-supply 914 can include a power plug to allow the computer 902 to be plugged into a wall socket or a power source to, for example, power the computer 902 or recharge a rechargeable battery.

There can be any number of computers 902 associated with, or external to, a computer system containing computer 902, with each computer 902 communicating over network 930. Further, the terms "client," "user," and other appropriate terminology can be used interchangeably, as appropriate, without departing from the scope of the present specification. Moreover, the present specification contemplates that many users can use one computer 902 and one user can use multiple computers 902.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present specification contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present specification can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 402.11 a/b/g/n or 402.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of embodiments have been described. Nevertheless, it will be understood that various modifications may be made without departing from the scope of the data processing system described herein. Accordingly, other embodiments are within the scope of the following claims.

What is claimed is:

1. A method for hydrocarbon phase behavior modeling for compositional reservoir simulation, the method comprising:

estimating phase properties of a hydrocarbon sample based on a mole-fraction weighted mixing rule;

determining contributions of individual phase components to the mole-fraction weighted phase properties;

generating input data for a machine learning model configured to perform phase identification and phase split determination in combination, the machine learning model including a first sub-network including a first number of layers each including respective neurons, and a second sub-network including a second number of layers each including respective neurons, the input data including the contributions from the individual phase components to the phase properties, wherein the first sub-network and the second sub-network are trained in parallel to enable the machine learning model to satisfy a performance threshold that indicates a recall threshold and a precision threshold;

generating, based on processing the input data using the neurons of the first number of layers of the first sub-network of the machine learning model, first output data including probability values for each potential phase state of the hydrocarbon sample, the probability values including a first value representing a liquid state for a grid block, a second value for a vapor state for the grid block, a third value for a two-phase state of the grid block, and a fourth value representing a critical state of the grid block;

processing the first output data including the probability values and the input data including the contributions from the individual phase components to the phase properties by the neurons of the second number of layers of the second sub-network of the machine learning model;

generating, by the second sub-network, second output data including fractional values for equilibrium of the individual phase components, vapor fraction, vapor compressibility, and liquid compressibility for the hydrocarbon sample; and outputting, for the grid block of a compositional reservoir simulation, the second output data, wherein the first output data and the second output data satisfy the performance threshold, wherein training the first sub-network and the second sub-network comprises:

receiving training data comprising phase properties values;

determining a categorical cross-entropy error from the first sub-network;

generating a probabilities vector based on the probability values and the categorical cross-entropy error;

processing the probability vector by the second sub-network;

determining, based on the processing, a mean-squared error (MSE) between predicted output values and output values of the output data; and training the first sub-network and the second sub-network simultaneously by minimizing the MSE value over a plurality of training epochs.

2. The method of claim 1, further comprising generating the training data comprising the phase properties values by performing operations comprising:

selecting a grid block for a simulated reservoir;

for the selected grid block:

generating input data of mole fractions based on a uniform distribution for pressure at a specified reservoir temperature;

determining a stability value and a split-phase value for the generated mole-fraction phase properties at each specified temperature and pressure;

determine a phase state value based on the stability value and the split-phase value; and generating one or more of a vapor fraction value, a vapor compressibility value, a liquid compressibility value, and liquid fraction value based on the phase state value.

3. The method of claim 1, wherein the input data further comprises a grid-block temperature, a grid-block pressure, and mole fractions data.

4. The method of claim 1, wherein the phase properties include a critical temperature, a critical pressure, a critical volume, an acentric factor, and a molecular weight value.

5. The method of claim 1, wherein the hydrocarbon sample represents one of a five component sample, a seven component sample, or a nine component sample.

6. The method of claim 1, wherein the machine learning model comprises a deep neural network (DNN) having at least three hidden layers and at least one output layer.

7. A data processing system for hydrocarbon phase behavior modeling for compositional reservoir simulation, the data processing system comprising:

at least one processor; and a memory storing instructions that, when executed by the at least one processor, cause the at least one processor to perform operations comprising:

estimating phase properties of a hydrocarbon sample based on a mole-fraction weighted mixing rule;

determining contributions of individual phase components to the mole-fraction weighted phase properties;

generating input data for a machine learning model configured to perform phase identification and phase split determination in combination, the machine learning model including a first sub-network including a first number of layers each including respective neurons, and a second sub-network including a second number of layers each including respective neurons, the input data including the contributions from the individual phase components to the phase properties, wherein the first sub-network and the second sub-network are trained in parallel to enable the machine learning model to satisfy a performance threshold that indicates a recall threshold and a precision threshold;

generating, based on processing the input data using the neurons of the first number of layers of the first sub-network of the machine learning model, first output data including probability values for each potential phase state of the hydrocarbon sample, the probability values including a first value representing a liquid state for a grid block, a second value for a vapor state for the grid block, a third value for a two-phase state of the grid block, and a fourth value representing a critical state of the grid block;

processing the first output data including the probability values and the input data including the contributions from the individual phase components to the phase properties by the neurons of the second number of layers of the second sub-network of the machine learning model;

generating, by the second sub-network, second output data including fractional values for equilibrium of the individual phase components, vapor fraction, vapor compressibility, and liquid compressibility for the hydrocarbon sample; and outputting, for the grid block of a compositional reservoir simulation, the second output data, wherein the first output data and the second output data satisfy the performance threshold, wherein training the first sub-network and the second sub-network comprises:

receiving training data comprising phase properties values;

determining a categorical cross-entropy error from the first sub-network;

generating a probabilities vector based on the probability values and the categorical cross-entropy error;

processing the probability vector by the second sub-network;

determining, based on the processing, a mean-squared error (MSE) between predicted output values and output values of the output data; and training the first sub-network and the second sub-network simultaneously by minimizing the MSE value over a plurality of training epochs.

8. The data processing system of claim 7, the operations further comprising generating the training data comprising the phase properties values by performing operations comprising:

selecting a grid block for a simulated reservoir;

for the selected grid block:

generating input data of mole fractions based on a uniform distribution for pressure at a specified reservoir temperature;

determining a stability value and a split-phase value for the generated mole-fraction phase properties at each specified temperature and pressure;

determining a phase state value based on the stability value and the split-phase value; and generating one or more of a vapor fraction value, a vapor compressibility value, a liquid compressibility value, and liquid fraction value based on the phase state value.

9. The data processing system of claim 7, wherein the input data further comprises a grid-block temperature, a grid-block pressure, and mole fractions data.

10. The data processing system of claim 7, wherein the phase properties include a critical temperature, a critical pressure, a critical volume, an acentric factor, and a molecular weight value.

11. The data processing system of claim 7, wherein the hydrocarbon sample represents one of a five component sample, a seven component sample, or a nine component sample.

12. The data processing system of claim 7, wherein the machine learning model comprises a deep neural network (DNN) having at least three hidden layers and at least one output layer.

13. One or more non-transitory computer readable media storing instructions for hydrocarbon phase behavior modeling for compositional reservoir simulation, the instructions, when executed by at least one processor, being configured to cause the at least one processor to perform operations comprising:

estimating phase properties of a hydrocarbon sample based on a mole-fraction weighted mixing rule;

determining contributions of individual phase components to the mole-fraction weighted phase properties;

generating input data for a machine learning model configured to perform phase identification and phase split determination in combination, the machine learning model including a first sub-network including a first number of layers each including respective neurons, and a second sub-network including a second number of layers each including respective neurons, the input data including the contributions from the individual phase components to the phase properties, wherein the first sub-network and the second sub-network are trained in parallel to enable the machine learning model to satisfy a performance threshold that indicates a recall threshold and a precision threshold;

generating, based on processing the input data using the neurons of the first number of layers of the first sub-network of the machine learning model, first output data including probability values for each potential phase state of the hydrocarbon sample, the probability values including a first value representing a liquid state for a grid block, a second value for a vapor state for the grid block, a third value for a two-phase state of the grid block, and a fourth value representing a critical state of the grid block;

processing the first output data including the probability values and the input data including the contributions from the individual phase components to the phase properties by the neurons of the second number of layers of the second sub-network of the machine learning model;

generating, by the second sub-network, second output data including fractional values for equilibrium of the individual phase components, vapor fraction, vapor compressibility, and liquid compressibility for the hydrocarbon sample; and outputting, for the grid block of a compositional reservoir simulation, the second output data, wherein the first output data and the second output data satisfy the performance threshold, wherein training the first sub-network and the second sub-network comprises:

receiving training data comprising phase properties values;

determining a categorical cross-entropy error from the first sub-network;

generating a probabilities vector based on the probability values and the categorical cross-entropy error;

processing the probability vector by the second sub-network;

determining, based on the processing, a mean-squared error (MSE) between predicted output values and output values of the output data; and training the first sub-network and the second sub-network simultaneously by minimizing the MSE value over a plurality of training epochs.

14. The one or more non-transitory computer readable media of claim 13, the operations further comprising generating the training data comprising the phase properties values by performing operations comprising:

selecting a grid block for a simulated reservoir;

for the selected grid block:

generating input data of mole fractions based on a uniform distribution for pressure at a specified reservoir temperature;

determining a stability value and a split-phase value for the generated mole-fraction phase properties at each specified temperature and pressure;

determining a phase state value based on the stability value and the split-phase value; and generating one or more of a vapor fraction value, a vapor compressibility value, a liquid compressibility value, and liquid fraction value based on the phase state value.

15. The one or more non-transitory computer readable media of claim 13, wherein the input data further comprises a grid-block temperature, a grid-block pressure, and mole fractions data.

16. The one or more non-transitory computer readable media of claim 13, wherein the phase properties include a critical temperature, a critical pressure, a critical volume, an acentric factor, and a molecular weight value.

17. The one or more non-transitory computer readable media of claim 13, wherein the hydrocarbon sample represents one of a five component sample, a seven component sample, or a nine component sample.

* * * * *